United States Patent [19]

Bar-Or et al.

[11] Patent Number: 5,055,389

[45] Date of Patent: Oct. 8, 1991

[54] DETECTION OF APPENDICITIS BY MEASUREMENT OF UROERYTHRIN

[75] Inventors: David Bar-Or, Denver; Stewart L. Greisman, Littleton; Jon G. Kastendieck, Denver, all of Colo.

[73] Assignee: Appenditech, Inc., Littleton, Colo.

[21] Appl. No.: 351,190

[22] Filed: May 4, 1989

Related U.S. Application Data

[63] Continuation-in-part of Ser. No. 84,565, Aug. 12, 1987, abandoned.

[51] Int. Cl.$^5$ .............................................. C12Q 1/00
[52] U.S. Cl. ........................................ 435/4; 435/18; 436/97; 436/147; 436/161; 436/164; 436/173; 548/519
[58] Field of Search ............... 436/164, 147, 161, 811, 436/908, 97, 173; 435/7, 4, 18, 7.1; 424/7.1; 548/519; 204/180.1, 186

[56] References Cited

PUBLICATIONS

Robbins, S., Pathologic Basis of Disease, (W. B. Saunders Company, Philadelphia 1974), p. 975.
Biological Abstracts 67(7): 40011, Min, Y., "Diagnosis and Treatment of Acute Appendicitis . . . ", Korean Cent J Med 33(1): 13–15, 1977.
Bile Pigment Fate in Gastrointestinal Tract, Seminars in Hematology, vol. 9, No. 1 (Jan.) 1972.
The Continuing Challenge of Hemoglobin and Bile Pigment Metabolism, Annuals of Internal Med., vol. 63, No. 6 (Dec. 1965).
Isolation and Identification of the Urinary Pigment Uroerythrin Eur. J. Biochem. 56, 230–244 (1975).
A Handbook of Routine Urinalysis, J. P. Lippincott Company, (Philadelphia) 1983 by Graff, SL. pp. 10–13, 83–84, 90.
Significance of Bile Pigment Determination in the Urine for the Differential Diagnosis of Appendicitis, Azerb. Med., Zh 0 (8), '86.
Clinical Pharmacology and Therapeutics, vol. 15(2), 1974.
Urinary Metabolites of Sodium Salicylate, Jour. Biol. Chem. vol. 145; 549–565, (1943).
N-Substituted Peptides in Urine in the Postoperative Period Bull. Acad. Pol. Soi. (Biol) vol. 13; 565–567, (1965).

Primary Examiner—Esther L. Kepplinger
Assistant Examiner—Carol A. Spiegel
Attorney, Agent, or Firm—Fields, Lewis, Pittenger & Rost

[57] ABSTRACT

Appendicitis can be detected by determining a threshold presence of the urinary pigment uroerythrin, in the urine of persons suspected of having appendicitis. The threshold presence of uroerythrin can be determined by precipitation of a sediment having a pink to red color. Additional qualitative, semiquantitative, or quantitative methods including HPLC (high pressure liquid chromatography), TLC (thin layer chromatography), radioimmunoassay, colorimetric tests, NMR (nuclear magnetic resonance), mass spectrometry, electrophoresis, monoclonal antibody tests, and other enzymatic tests may also be employed to measure uroerythrin levels.

8 Claims, No Drawings

DETECTION OF APPENDICITIS BY MEASUREMENT OF UROERYTHRIN

This application is a continuation-in-part of our co-pending U.S. patent application Ser. No. 084,565, filed Aug. 12, 1987, now abandoned.

TECHNICAL FIELD

This invention relates to methods for determining levels of uroerythrin in urine above a threshold value of about $2 \times 10^{-4}$ mg/cc as indicative of detecting appendicitis. These methods include a variety of procedures for this measurement including precipitation of uroerythrin adsorbed to urates as well as a number of instrumental procedures described in detail later in this disclosure.

The diagnosis of appendicitis often challenges a physician's ability to differentiate this disease from other abdominal or pelvic disorders such as abdominal aortic aneurysm, pelvic inflammatory disease, ectopic pregnancy, ruptured or perforated viscus, gastrointestinal bleeding, hemorrhage pancreatitis, perforated diverticulum, ovarian abscess, Crohn's disease, mesenteric adenitis and intestinal obstruction. Were it not for the fact that such diseases often simulate appendicitis, and the fact that a fully developed picture is seldom available to the physician, a diagnosis of appendicitis would be relatively straightforward: confirmation of periumbilical pain of less than 72 hours' duration, migration of such pain to the right lower quadrant in a patient with a temperature of 99.5° to 101.3° F., evidence of abdominal tenderness, rigidity, a right-lower-quadrant mass and the presence of a mass on rectal examination.

(The diagnostic indicators described above, when found, are representative for patients later described in this submission as "suspected of having appendicitis".) In many respects, negative predictors of appendicitis are often more helpful in excluding appendicitis from a diagnosis. The most commonly employed negative predictors include: symptoms lasting more than 72 hours, pain at locations other than those noted above, temperature below 99.5° or above 101.3° C. and the absence of anorexia. Unfortunately, neither leukocyte counts nor roentgenograms are sensitive or specific to appendicitis; and no reliable chemical tests have heretofore been developed.

Hence, diagnosis of appendicitis is made almost solely on those clinical grounds noted above. Consequently, a large number of patients are taken to the operating room for explorative operations, with an average false positive experience of about 20%. This rather high false positive experience is tolerated because prompt action is needed to prevent this acute disease, curable by appendectomy, from advancing to one complicated by perforation, peritonitis, long-term sequelae, and even death.

BACKGROUND ART

The prior art has recognized that the presence, or the absence, of certain bile pigments might be used as indicators of the existence of certain disease states. For example, the article, *Bile Pigment Fate in Gastrointestinal Tract*, Seminars in Hematology, Vol. 9, No. 1 (January) 1972, points out that the presence of fecal bile pigments, which can also be detected in the urine, can be used to help diagnose certain diseases, particularly those of the liver. Such diagnoses are based upon the understanding that urobilinogen is produced in the gut from bilirubin excreted from the liver into the bile; and that when it is diseased, the liver's excretory capacity for urobilinogen is greatly reduced. Consequently, more urobilinogen reaches systemic circulation. It is now generally believed that this, in turn, is due to increased anastomoses between the portal and systemic vessels as well as decreases in the number and function of hepatocytes. There also appears to be evidence that bilirubin and urobilinogen share a mechanism for hepatic uptake. Hence, competition between increased amounts of bilirubin and urobilinogen for hepatic uptake are also thought to contribute to urobilinogenuria associated with hemolytic disorders. In any event, the above noted reference lists the following conditions which may lead to alterations of urinary urobilinogen concentrations:

| Factors Influencing Urinary Urobilinogen Concentration | Conditions in Which Urinary Urobilinogen Tends to Increase | Conditions in Which Urinary Urobilinogen Tends to Decrease |
|---|---|---|
| Amount of bilirubin conjugate entering gut | Increased e.g., hemolytic states | Decreased e.g., obstruction of common bile duct |
| Loss of bile pigment from gut | | Biliary fistula; small bowel fistula |
| Alterations in gut flora | Biliary tract infection; colonization of small bowel | Suppression of gut flora by antibiotics; most common in newborn treatment |
| Alteration in transmit time through gut | Constipation | Severe diarrhea |
| Excretion of urobilinogen by liver | Decreased due to hepatocellular disease, transhepatic shunting of portal blood; competition with other substances; e.g., bilirubin | |
| Renal factors | Decrease in urine volume | Decrease glomerular filtration rate; increase in urine volume |

It is also known that a change in the color of feces is usually present in the case of biliary obstruction and that this color change also is related to urobilinogen concentration. Hence the daily excretion of urobilinogen has been used to assess the degree of obstruction. For example, it is known that the average daily fecal excretion of urobilinogen in normal individuals is about 140 mg (range 40–280 mg day) although there is wide variation in reported values. Males excrete significantly more urobilinogen than females even when expressed on a weight basis (females, typically 0.61 mg/kg body weight/day; males, typically 0.90 mg/kg body weight/day; mean SD). Moreover, these values fluctuate from day to day. However, lower levels (5 mg/24 hour in adults) are found when there is prolonged total obstruction of the biliary tract.

On the other hand, it is also known that in a variety of other disease states there is a surplus rather than a deficit of fecal urobilinogen in relation to the rate of destruction of mature circulating red blood cells and their hemoglobin. This surplus, at times quite large, is represented by what is now generally known as the "early labeled" bile pigment, that fraction of the total bile pigment, bilirubin, or urobilinogen, that exhibits isotopic labeling within a few days after administration of $15_N$ or $14_C$ labeled glycine. This is in contrast to the normally much larger fraction (85 to 90%) that exhibits its peak labelling in relation to the destruction of hemoglobin of mature circulating red blood cells in the period of 110 to 130 days after administration of labeled glycine. However, as noted in *The Continuing Challenge of Hemoglobin and Bile Pigment Metabolism*, Annals of Internal Medicine, Vol. 63, No. 6 (December) 1965, even though there is a presumed relationship of bile bilirubin and fecal urobilinogen to the destruction of hemes, the amount of bilirubin formed from destroyed hemoglobin has not been represented quantitatively in the excreta by recognizable derivatives such as urobilinogen. Among the known pigments (e.g., bile pigments, porphyrins, hemoglobin, indole derivatives, flavins, melanins and pteridins) which may be excreted in human urine there are groups of yellow, brown, and red pigments, generally designated as urochromes, whose chemical structures are still not totally understood. This lack of understanding is due, at least in part, to the highly labile nature of such pigments. Moreover, increased amounts of uroerythrin have been postulated in certain diseases. For example, an article entitled, *Isolation and Identification of the Urinary Pigment Uroerythrin*, Eur. J. Biochem. 56, 239-244 (1975) teaches: (1) that the red pigment uroerythrin is absorbed by the amorphous urate sediments (sedimentum lateritium), (2) that increased amounts of uroerythrin are observed in patients in certain pathological states (e.g., diseases of the liver) and (3) that uroerythrin most probably has a chemical structure which is based upon a tripyrrole system. This reference does not however correlate the presence of appendicitis with a threshold presence of uroerythrin or any other bile pigment.

Graff, in *A Handbook of Routine Urinalysis*, J. P. Lippincott Company, (Philadelphia) 1983, cites that large amounts of uroerythrin can occur in acute febrile disease. However, clinical data generated while developing the instant invention includes many cases where patients with appendicitis presented without fever, yet exhibited high levels of uroerythrin (above the threshold of $2 \times 10^{-4}$ mg/cc), as confirmed both by instrumental data and induction of the pink to red precipitate described in this disclosure. In addition, many patients without appendicitis, yet having a fever, showed uroerythrin levels below threshold and produced urine samples in which the pink to red precipitate was absent. Clearly this data demonstrates that fever alone is not responsible for creation of high levels of uroerythrin and formation of the pink to red precipitate. Further, the use of pink to red precipitate as an indicator of uroerythrin levels above threshold and thus indicative of appendicitis is valid even under conditions where other red substances are formed in the urine, since all other known disease states causing red coloration present with clinical symptoms different than those in appendicitis, and in most cases have chronic symptomology rather than acute symptomology (e.g., porphyrrhea).

Abasov, in *Significance of Bile Pigment Determination in the Urine for the Differential Diagnosis of Appendicitis*, Azerb.Med., Zh 0 (8), 1986, p. 11-13, used the presence of certain bile pigments in the urine as an indicator of viral hepatitis, thereby eliminating appendicitis as the disease state in question, but made no correlation between presence of a given pigment and a positive diagnosis of appendicitis.

Uroerythrin has been isolated from human urine and purified as its trimethyl derivative. For example, the previously cited article, *Isolation and Identification of the Urinary Pigment Uroerythrin*, Eur. J. Biochem. 56 (1975), teaches a purification method based upon introduction of urine into a column of an ion exchange resin such as Amberlite XAD-2 resin which absorb the uroerythrin. Purification is then obtained through conversion of the uroerythrin into its trimethyl derivative and chromatography on silica gel thin-layer plates.

DISCLOSURE OF THE INVENTION

The methods and procedures of this patent disclosure are based upon Applicant's qualitative and quantitative findings regarding the presence of uroerythrin and derivative tripyrrole compounds, in the urine of human beings suffering from appendicitis. Applicants have established a definite correlation between a threshold presence of uroerythrin (in solution) found in human urine and the presence of appendicitis. This threshold presence is at or above about $2 \times 10^{-1}$ mg/cc. This correlation has been clinically tested and proven valid.

Applicants have developed procedures to induce precipitation of uroerythrin adsorbed onto urates, giving a pink to red sediment when uroerythrin levels are above the threshold value. These procedures for inducing precipitation of the pink to red sediment, elucidated in further detail throughout this disclosure, represent the first part of the instant invention.

In urine samples containing uroerythrin levels above the threshold such that precipitation can be induced as described below, actual levels of uroerythrin in solution have been confirmed by definitive quantitative techniques including HPLC, spectrophotometric colorimetry and mass spectrometry. Verification of levels of uroerythrin in urine at or greater than the threshold value of $2 \times 10^{-4}$ mg/cc and measurement of such levels to validate a condition of appendicitis through techniques such as HPLC, TLC, mass spectrometry, monoclonal antibodies, spectrophotometric colorimetry, radioimmunoassay, NMR, electrophoresis and enzymatic tests represents the second part of the invention.

Initial precipitation of the pink to red sediment can be induced as the temperature of the urine sample drops from human body temperatures near 98.6° F. to temperatures below about 65° F. The precipitation is even more pronounced as the temperature falls into a range of about 35° to 60° F. Uroerythrin itself is moderately labile in the presence of light; however, once precipitation is induced with the uroerythrin adsorbed to urates, the sediment is reasonably stable. To maximize accuracy of the tests disclosed, it is recommended that the tests should be conducted in less than 30 minutes after the urine sample is obtained. A temperature drop aided by the use of refrigeration, is therefore a highly preferred version of our test. For example, placement of a urine sample under refrigeration at about 40° F. for about 10 to 20 minutes is a highly preferred refrigeration aided test protocol. However, the urine sample generally should be sufficiently concentrated (e.g., specific gravity > 1.010) to produce a pronounced precipitate.

Qualitative detection of the threshold presence of uroerythrin, (i.e., above about $2 \times 10^{-4}$ mg/cc) through induced precipitation of uroerythrin can be brought about and enhanced by various procedures hereinafter more fully described. For example, the pink to red precipitate can be produced through acidification of the urine sample to a pH of less than about 4. For example, the acidification may employ 1.0M HCl and EDTA (or other salts) to produce a precipitation in less than about 5 minutes. Crystallization procedures whereby an organic solvent is added to the urine sample (e.g., methanol) can also be employed to enhance precipitation. It should be specifically noted that when such chemical precipitation procedures are employed, it is not necessary to refrigerate the sample. However, the chemical precipitation procedures (acidification, crystallization etc.) may be augmented by refrigeration in many instances. Obviously, once precipitation of the pink to red sediment is induced, threshold levels for uroerythrin have been established, so additional steps further enhancing precipitation are unnecessary but are not detrimental. Furthermore, levels of uroerythrin can be specifically determined and confirmed by various other physical and/or chemical procedures. These other procedures include, but are not limited to: HPLC, TLC, spectrophotometric colorimetry, monoclonal antibody techniques, radioimmunoassaying, enzymatic (biologic) procedures, electrophoresis, NMR and mass spectrometry. Those skilled in the art will appreciate that uroerythrin levels in urine samples can be determined by comparing test data to calibration curves created for each individual test using uroerythrin standard samples of known concentration. These calculated uroerythrin levels from urine samples can establish levels above threshold (i.e., $2 \times 10^{-4}$ mg/cc) and hence are indicative of the presence of appendicitis.

BEST MODE FOR CARRYING OUT THE INVENTION

The following procedures and exemplary tests are presented as illustrations of our methods for testing for appendicitis in human beings. These tests are intended to illustrate the concept of this invention, but they should in no way be regarded as limitations upon the concept.

1. Clinical Validation

One hundred twenty three consecutive uroerythrin tests were performed on urine samples of patients (most of these patients were seen at Swedish Medical Center, Englewood, Colorado) who had a urinalysis as part of their clinical evaluation of abdominal pain (where appendicitis was suspected). Test results were reviewed for specificity and sensitivity. Although it is well known that the number of false positives and false negatives will vary between populations having differing prevalence of the disease, and this test group was all suspected of having appendicitis, the test group data generated here is nevertheless relevant since the test described here would typically only be used on patients suspected of having appendicitis after standard clinical evaluation. Precipitation tests without chemical enhancement were employed. A test was considered positive when a pink to red sediment was identified in response to cooling. With respect to these patients:
28/123 were true positives (test positive and surgery positive)
1/123 was false negative (test negative and surgery positive)
2/123 were false positives (test positive and surgery negative)
92/123 were true negatives (test negative and surgery negative or not required)

$$\text{Sensitivity} = \frac{\text{true positives}}{\text{true positives} + \text{false negatives}} = \frac{28}{28 + 1} = 96.5\%$$

$$\text{Specificity} = \frac{\text{true negatives}}{\text{true negatives} + \text{false positives}} = \frac{92}{92 + 2} = 97.4\%$$

These results clearly support our discovery.

2. Precipitation Tests

Precipitation is the easiest qualitative method of identifying threshold levels of uroerythrin in urine. Applicants have found that urine of persons with appendicitis will precipitate a pink to red sediment, when the temperature of the urine sample is lowered within about 30 minutes after the urine sample is taken. The temperature lowering process can be speeded up without loss of sensitivity by refrigerating the urine sample. Refrigeration temperatures in the range of about 35° to about 60° F. are preferred. Preferably the sample should be subjected to such temperatures within about 30 minutes from the time the sample is obtained. The refrigeration step can be most conveniently carried out at about 40° F. for from about 5 to about 15 minutes. The pink to red uroerythrin sediment is readily identifiable from any other sediments in the precipitate when uroerythrin is present at or above the threshold level. In other words the threshold level is that level which will produce the pink to red precipitate when the urine sample's temperature is lowered to the range of about 35° to about 60° F. within 30 minutes after the sample is taken. By virtue of its color alone, as seen by the naked eye, the sediment is identifiable without additional preparation of the urine sample. Again, however, the color can be related to a preestablished color chart which correlates the color of the sample to the existence of appendicitis. Analogous preestablished levels (numerical concentrations etc.) can be established for all the various detection methods, e.g., HPLC, TLC, NMR, monoclonal antibody etc. which can be employed to measure uroerythrin levels in a urine sample.

For example, the addition of about 0.4 cc of buffer phosphate, at a pH of about 4.0, and 1 to 5 milligrams of NaCl and 1 to 5 milligrams of potassium urate, to about 5-10 cc of urine will greatly enhance precipitation of the pink to red sediment from the urine sample when appendicitis is in fact present. Refrigeration will further hasten this chemical precipitation. Another chemical technique for enhancing such a precipitation is to acidify the urine sample to a pH of about 2.0 with 1 molar HCl, then add 0.1 gram of EDTA, (ethylenediamine tetraacetic acid) and finally stir and centrifuge. Again, no refrigeration is required but likewise, it may enhance this particular acid precipitation technique.

Again, those skilled in this art will appreciate that many other tests may be employed to detect the presence of and, if need be, the concentration of, uroerythrin in urine; NMR, HPLC, TLC, spectrophotometric colorimetry, monoclonal antibody, radioimmunoassay enzyme, electrophoresis and mass spectrometry tests are the most readily employable tests. Liquid chromatography (e.g., HPLC and TLC) are the more preferred methods for determining the concentration of uroerythrin in the urine sample. Specific representative techniques with respect to some of these possible techniques are given in later sections of this patent disclosure.

Some of the results and procedures used to establish the invention were as follows:

I. THE PRECIPITATE'S PHYSICAL PROPERTIES

A. The pink to red precipitate is soluble in water.
B. It is insoluble in weak acids.
C. It is slightly soluble in methanol.
D. It is slightly soluble in acetonitrile.
E. It is insoluble in hexane.
F. It is insoluble in methylene chloride.

Conclusion: The pink to red sediment contains mainly polar compounds. Following the establishment of this observation, procedures were developed to isolate the material from the urine.

II. URINE EXTRACTION PROCEDURE

1. A C18 disposable (octadecyl silane such as Bond Elut, 3 cc) column was used.
2. The column was primed with 2 cc methanol, followed by 2 cc water.
3. 5 cc of urine were mixed with 5 cc buffer phosphate (1M, pH 3.0).
4. The column was washed with 2 cc water.
5. The wash contaminants and other bands were washed with 1 cc of 40% methanol and 60% 0.01M phosphate buffer, pH 2.5.
6. The material was eluted and collected in 1 cc of methanol.
7. The elution fluid was analyzed.

The eluted fluid has a red-orange color. Even though HPLC was employed, TLC could have been just as well utilized.

III. CONDITIONS FOR HPLC ANALYSIS

Solvents:
  60% Buffer Phosphate 0.01M, pH 2.5
  30% Acetonitrile
  10% Methanol
Column: C-18 Micro Pak MCH-5 END CAPPED, 15 cm $\times$ 4 mm i.d.
Column Temperature: 95° F.
Detector: UV/VIS at 490 nm
Flow Rate: 1.5 cc/minute Results of HPLC analysis under the above conditions reveal a peak at around 9 minutes. This peak was collected and its absorbance spectrum analyzed. The absorbance spectrum reveals 3 LAMBDA maxima at 269, 325 and 490. These figures are in accordance with the LAMBDA maxima for uroerythrin in the *Eur. J. Biochem* reference previously cited.

Since other peaks appeared in the chromatogram, and in order to verify the carboxylic groups of uroerythrin, the extraction procedure was repeated and HPLC run at a pH 7.0. Since at this pH the carboxylic groups will be ionized, uroerythrin will not be retained on the C18 column and hence the suspect peak was eliminated at 9 minutes, but not the other peaks; this again suggests that the material is uroerythrin. By using the same extraction procedure on sediment that was dissolved in water, it was determined that the pink to red sediment contains uroerythrin but at a lesser concentration than in urine.

In the extraction process, a red band in the C18 column was observed. It was removed physically by cutting it from the column. When analyzed by HPLC, it revealed uroerythrin.

After repeated injections of the same extract containing uroerythrin to the HPLC, a marked decrease in uroerythrin concentration was observed. It was also determined that uroerythrin is most probably somewhat labile in the presence of light.

IV. PREPARATION OF STANDARD FOR HPLC

1. Pass 20 cc of urine of a patient with appendicitis through a C18 column (octadecyl silane such as Bond Elut, 3 cc).
2. Wash with 10 cc water.
3. Wash with 10 cc 20% methanol/80% phosphate buffer, 1M, pH 3.0.
4. Wash with 10 cc 40% methanol/60% phosphate buffer, 1M, pH 3.0.
5. Cut red band.
6. Dissolve in methanol.
7. Filter out the C18 material.
8. Dilute with water and reconcentrate on a second C18 column.
9. Elute with methanol.
10. Inject into HPLC.
11. Determine purity.
12. Evaporate to dryness and weigh.
13. Purity $\times$ weight = amount of uroerythrin in that peak.

V. PRECIPITATION PROCEDURE WITHOUT REFRIGERATION

1. Start with 10–20 cc of urine.
2. Acidify to pH 2.0 with 1.0M HCl.
3. Add 0.1 gm EDTA.
4. Let stand for 5 minutes, preferably with stirring or centrifuging.

VI. COLOR TEST OF C18 COLUMN

After elimination of all other contaminants by a purification process, but before elution, a color reaction with uroerythrin carboxylic group can be done. This can be done either by a pH indicator or by substituting the carboxyl group with other groups to generate a color reaction proportionate to the amount of uroerythrin.

Those skilled in the art will appreciate that the conditions employed in these various tests will be those appropriate to the particular precipitation agents being used. Thus, while the invention has been described by specific examples and preferred embodiments, there is no intent to limit the inventive concept which is set forth in the following claims.

We claim:

1. A method for diagnosing acute appendicitis comprising the steps of:
  obtaining a urine sample, having a specific gravity greater than 1.010, from a human being suspected of having appendicitis by virtue of nausea, vomiting or anorexia in association with abdominal pain, which characteristically will be present in the periumbilical or right lower quadrant area;
  inducing precipitation of pink to red colored sediment from the urine sale in less than about 30 minutes from the time the sample is taken; and
  testing the precipitated sediment to detect a concentration of uroerythrin equal to or greater than $2 \times 10^{-4}$ mg/cc to confirm a diagnosis of appendicitis.

2. A method for diagnosing appendicitis, as claimed in claim 1, wherein:
  the testing comprises one or more methods selected from the group consisting of temperature induced precipitation, acid induced precipitation, HPLC, TLC, spectrophotometric colorimetry, color chart comparison, enzymatic tests, NMR, mass spectrometry, and electrophoresis.

3. A method for diagnosing acute appendicitis comprising the steps of:
obtaining a urine sample, having a specific gravity greater than 1.010 from a human being suspected of having appendicitis by virtue of nausea, vomiting or anorexia in association with abdominal pain, which characteristically will be present in the periumbilical or right lower quadrant area;
lowering the temperature of the urine sample to reach a temperature of less than about 65° F. in less than about 30 minutes from the time the sample is taken to induce the precipitation of a pink to red colored sediment; and
testing the precipitated sediment to detect a concentration of uroerythrin equal to or greater than $2 \times 10^{-4}$ mg/cc to confirm a diagnosis of appendicitis.

4. A method for diagnosing appendicitis, as claimed in claim 3, wherein:
the temperature of the urine sample is lowered to a temperature of between about 35° to about 60° F. in a period from about 5 to 20 minutes from the time the sample is taken.

5. A method for diagnosing appendicitis, as claimed in claim 4, wherein the testing comprises
establishing a color chart which correlates the color of the precipitate to preestablished color levels which are indicative of uroerythrin having a concentration equal to or greater than $2 \times 10^{-4}$ mg/cc; and
comparing the color of the sediment to the color chart to determine if the color comparison indicates a concentration of uroerythrin equal to or greater than $2 \times 10^{-4}$ mg/cc thereby confirming the presence of appendicitis.

6. A method for diagnosing acute appendicitis comprising the steps of:
obtaining a urine sample, having a specific gravity greater than 1.010 from a human being suspected of having appendicitis by virtue of nausea, vomiting or anorexia in association with abdominal pain, which characteristically will be present in the periumbilical or right lower quadrant area;
acidifying the urine sample to a pH below 4 to induce precipitation of pink to red colored sediments from the urine; and
testing the precipitated sediment to detect a concentration of uroerythrin equal to or greater than $2 \times 10^{-4}$ mg/cc to confirm a diagnosis of appendicitis.

7. A method for diagnosing appendicitis, as claimed in claim 6, wherein the testing comprises
establishing a color chart which correlates the color of the precipitate to preestablished color levels which are indicative of uroerythrin having a concentration equal to or greater than $2 \times 10^{-4}$ mg/cc;
separating the sediment from the remainder of the urine sample; and
comparing the color of the sediment to the color chart to determine if the color comparison indicates a concentration of uroerythrin equal to or greater than $2 \times 10^{-4}$ mg/cc thereby confirming the presence of appendicitis.

8. A method for diagnosing acute appendicitis comprising the steps of:
obtaining a urine sample, having a specific gravity greater than 1.010 from a human being suspected of having appendicitis by virtue of nausea, vomiting or anorexia in association with abdominal pain, which characteristically will be present in the periumbilical or right lower quadrant area;
mixing 10-20 cc of the urine sample with sufficient 1.0 HCl to bring the sample to a pH of about 2.0;
adding about 0.10 gm EDTA;
letting the acidified sample stand for about 5 minutes to form a pink to red colored sediment; and
testing the precipitated sediment to detect a concentration of uroerythrin equal to or greater than $2 \times 10^{-4}$ mg/cc to confirm a diagnosis of appendicitis.

* * * * *